United States Patent [19]

Hunter

[11] Patent Number: 5,668,301

[45] Date of Patent: Sep. 16, 1997

[54] METHOD AND APPARATUS FOR THE DETECTION OF HYDROGEN USING A METAL ALLOY

[75] Inventor: Gary W. Hunter, Avon, Ohio

[73] Assignee: The United States of America as represented by the Administrator of the National Aeronautics and Space Administration, Washington, D.C.

[21] Appl. No.: 621,028

[22] Filed: Mar. 22, 1996

Related U.S. Application Data

[62] Division of Ser. No. 366,645, Dec. 30, 1994, Pat. No. 5,520,753.

[51] Int. Cl.$^6$ .......................... H01L 29/66; G01N 27/26
[52] U.S. Cl. .................. 73/23.2; 73/31.06; 324/71.5; 324/69.3; 29/610.1; 29/25.01; 422/83; 422/98; 338/34; 436/151
[58] Field of Search .................. 73/23.2, 31.06, 73/31.02, 31.03; 324/719, 693, 71.5; 29/610.1, 25.01; 338/34; 422/83, 98; 420/463; 436/151

[56] References Cited

U.S. PATENT DOCUMENTS

| | | | |
|---|---|---|---|
| 4,058,368 | 11/1977 | Svensson et al. | 23/254 E |
| 4,139,373 | 2/1979 | Notton | 75/175.5 |
| 4,313,907 | 2/1982 | McNally | 422/97 |
| 4,536,196 | 8/1985 | Harris | 55/16 |
| 4,587,104 | 5/1986 | Yannopoulos | 422/94 |
| 4,719,081 | 1/1988 | Mizuhara | 420/463 |
| 4,728,580 | 3/1988 | Grasselli et al. | 428/610 |
| 4,792,433 | 12/1988 | Katsura et al. | 422/98 |
| 4,892,834 | 1/1990 | Rauh | 436/149 |
| 4,931,851 | 6/1990 | Sibbald et al. | 357/25 |
| 4,977,658 | 12/1990 | Awano et al. | 29/25.01 |
| 5,018,380 | 5/1991 | Zupanicic et al. | 73/23.2 |
| 5,028,394 | 7/1991 | Lowell, Jr. et al. | 422/58 |
| 5,086,286 | 2/1992 | Yasukawa et al. | 338/34 |
| 5,223,783 | 6/1993 | Wilis | 324/71.5 |
| 5,279,795 | 1/1994 | Hughes et al. | 422/98 |
| 5,389,340 | 2/1995 | Satake | 422/98 |
| 5,417,821 | 5/1995 | Pyke | 204/153.1 |
| 5,448,906 | 9/1995 | Cheung | 73/31.06 |
| 5,520,753 | 5/1996 | Hunter | 148/430 |

*Primary Examiner*—Hezron E. Williams
*Assistant Examiner*—J. David Wiggins
*Attorney, Agent, or Firm*—Kent N. Stone; Susan D. Reinecke

[57] ABSTRACT

A hydrogen sensitive metal alloy contains palladium and titanium to provide a larger change in electrical resistance when exposed to the presence of hydrogen. The alloy is deposited on a substrate and a thin film and connected across electrical circuitry to provide a sensor device that can be used for improved sensitivity and accuracy of hydrogen detection.

18 Claims, 1 Drawing Sheet

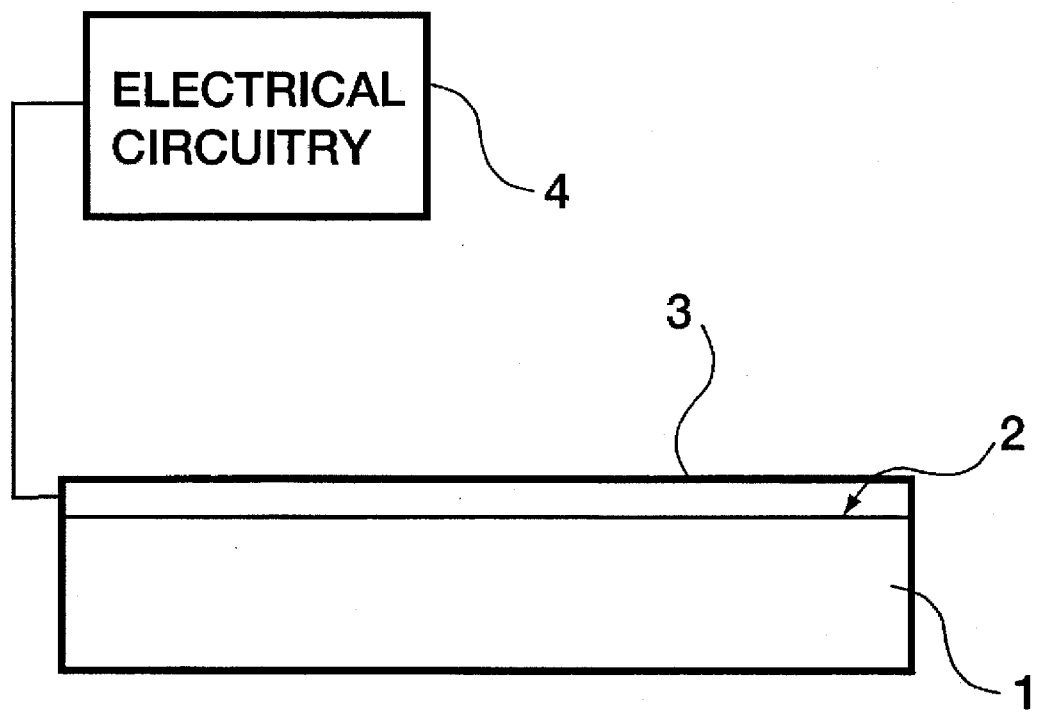

METHOD AND APPARATUS FOR THE DETECTION OF HYDROGEN USING A METAL ALLOY

This is a divisional of application(s) Ser. No. 08/366,645 filed on Dec. 30, 1994, which is now U.S. Pat. No. 5,520,753.

ORIGIN OF THE INVENTION

The invention described herein was made by an employee of the U.S. Government and may be manufactured and used by or for the U.S. Government without the payment of any royalties thereon or therefor.

FIELD OF THE INVENTION

This invention relates to a PdTi alloy in general and more particularly to a hydrogen sensitive PdTi metal alloy for use in hydrogen sensitive applications, such as hydrogen sensitive resistors, metal oxide semiconductor field effect transistors (MOSFET) and Schottky diode structures.

BACKGROUND

Providing a material that can accurately detect the presence of hydrogen or hydrocarbons is desirable. Hydrogen sensitive metals undergo a change (e.g., a change in resistance) that can be detected when interacting with hydrogen. For example, as hydrogen dissociates on a surface of a metal and migrates into the interior of the metal, the electrical resistance of the metal is changed. Usually, this increases the electrical resistance of the metal. Similarly if the hydrogen dissociates on the surface of a metal that is part of an electrical circuit, then the electrical properties of the entire circuit are affected.

Several metals and metal alloys have applications as hydrogen sensitive metals. Palladium and alloys of palladium containing silver (for example, PdAg) are known hydrogen sensitive metals. It is known to use a palladium resistor as a hydrogen sensor. The resistor is formed by depositing palladium on a substrate. As hydrogen is absorbed by the palladium, the resistance of the metal changes. The change in resistivity can then be detected (e.g., by an electrical circuit connected to the palladium resistor). Additionally, it is known to use Pd or PdAg as a gate in a MOSFET or Schottky diode device. The detection of hydrogen by the gate triggers changes in the electronic properties of the device.

In both of these applications, the Pd and PdAg are sensitive to the presence of hydrogen. The use of these materials, however, does have limitations. For instance, in the palladium resistor as the palladium dissociates and absorbs hydrogen, the palladium undergoes a phase transformation. This causes hysteresis. Furthermore, this phase transformation may damage the layer of palladium. Similarly, the PdAg film experiences a phase transformation. This occurs at higher concentrations of hydrogen. The presence of the silver does, however, reduce damage to the film because the film is more resilient.

It is desirable for a hydrogen sensitive metal in the presence of hydrogen to experience a large change in resistivity without .undergoing a phase transformation. Furthermore, it is desirable for the change to be repeatable (i.e., the sensing metal can be used for multiple exposures to hydrogen).

This has been considered by Hughes et al., in "Wide Range $H_2$ Sensor Using Catalytic Alloys," presented at the 183rd Meeting of the Electrochemical Society, May 1993. Hughes et al. used an alloy of palladium and nickel, particularly Pd13%Ni, as a hydrogen sensitive resistor. This material experienced nearly a 10% change in resistance when exposed to an environment consisting of 100% hydrogen. Additionally, the Pd13%Ni alloy did not undergo a phase transformation and is repeatable. The use of Pd13%Ni alloy as a hydrogen resistor, however, is limited because the alloy experiences a small change in resistance at low amounts of hydrogen (e.g., when exposed to an environment consisting of 10% hydrogen, the change in resistance is small, approximately 1%).

Small changes in resistance may also be attributed to fluctuations in temperature. As a result, it is undesirable to use a material which experiences only a small change in resistance (e.g., less than 1%, as for example, exhibited by the Pd13%Ni alloy) when exposed to low amounts of hydrogen because the change of resistance is similar to those changes caused by temperature fluctuations. It would be difficult to determine whether the change in resistance is a result of the presence of hydrogen or a fluctuation in temperature. Unless strict temperature control of the resistor is possible, these materials are not acceptable for detecting small amounts of hydrogen.

An alloy of palladium and chromium, particularly Pd13%Cr, has been tested as a hydrogen sensitive resistor. The Pd13%Cr alloy also did not undergo a phase transformation when .exposed to a hydrogen environment. Additionally, the detection of hydrogen is repeatable. The Pd13%Cr alloy, however, experiences only a 1% change in resistance when exposed to an environment of 100% hydrogen. The use of this material in this form would therefore be unacceptable at both low and high concentrations of hydrogen for reasons discussed above.

Further, the number of alloys available for hydrogen detection is limited. Each alloy has its own sensitivity to hydrogen, hydrocarbons, and poisons. It is desirable to have a wide range of alloys available to enable detection of hydrogen bearing gases in a wide variety of environments and temperatures.

Metal alloys containing palladium and titanium are known. For example, U.S. Pat. No. 4,082,900 to Shimogori et al. discloses a Ti—Pd alloy containing 0.1 to 0.2% of palladium. The addition of palladium reduces crevice corrosion and embrittlement by absorbing hydrogen.

U.S. Pat. No. 4,139,373 to Norton discloses a Ti alloy containing another metal such as palladium. The alloy consists of 60 to 94 weight % Ti and 6 to 40 weight % of at least one additional metal which includes palladium. The addition of palladium to the alloy reduces the corrosion rate and improves the electrical conductivity.

U.S. Pat. No. 4,536,196 to Harris discloses alloy coated with a layer of titanium. A membrane of the alloy with the titanium coating is used for diffusing hydrogen from a mixture of gases.

U.S. Pat. No. 4,666,666 to Taki et al. discloses a Ti alloy having small amounts of Pd (i.e., between 0.005% to 2.0% by weight ). The alloy has improved corrosion resistance and improved resistance to hydrogen absorption.

U.S. Pat. No. 4,719,081 to Mizuhara discloses a Pd alloy containing Ti for use in joining ceramic metals. The alloy includes 65 to 98 weight % palladium, 1 to 20% nickel, 0.5 to 20% chromium, 0.5 to 10 weight % Ti or Zr and 0 to 10% molybdenum.

U.S. Pat. No. 4,728,580 to Grasselli et al. discloses an amorphous metal alloy that may contain Pd and Ti. The alloy is used for reversible hydrogen gas storage.

None of the above mentioned U.S. patents, however, disclose the use of a PdTi metal alloy as a hydrogen sensor.

SUMMARY OF THE INVENTION

To solve the above and other problems, the present invention is directed to a hydrogen sensitive metal alloy containing palladium and titanium that has an increased change in electrical resistance in the presence of hydrogen. The PdTi alloy will not undergo a phase transformation when exposed to an environment of hydrogen. Furthermore, the hydrogen sensitive PdTi alloy will experience a change in resistance upon exposure to hydrogen. This resistance change is present even after repeated exposure to environments containing, hydrogen The titanium in the palladium acts as trapping sites for hydrogen. This reduces the diffusion of hydrogen through the alloy and yields a larger change in resistance in the presence of hydrogen. Further, Ti absorbs oxygen. As hydrogen enters the metal, it reacts with the oxygen the Ti and removes the oxygen from the alloy. This effect also changes the resistance of the alloy. Therefore, the sensitivity of the alloy comes from both hydrogen being absorbed by the Pd but also oxygen being removed from the Ti.

A thin film material of the hydrogen sensitive PdTi metal alloy in accordance with embodiments of the present invention may be prepared by sputtering the palladium and titanium from multiple or single targets. Atomic particles of palladium and titanium are propelled onto a substrate to form a thin film of the alloy. This technique produces an alloy having a fine grain size. Other methods may also be employed to form the alloys (e.g., electron beam evaporation, thermal evaporation, etc.). After formation of the PdTi alloy, it may be annealed to improve homogeneity of the alloy (i.e., to ensure that the palladium and titanium are evenly distributed throughout the .alloy) as well as remove impurities from the surface of the film. Furthermore, the alloy may also be produced in other forms (e.g., bulk materials such as wire). These can be formed using numerous methods (e.g., extrusion and drawing).

A thin film of the PdTi alloy according to the present invention is preferably sputtered then annealed. The alloy displays a change in resistance up to 18% when exposed to concentrations Of hydrogen. This change in resistance is a considerable improvement over the resistance changes of the known hydrogen sensitive materials.

BRIEF DESCRIPTION OF THE DRAWING

The sole FIGURE schematically depicts a hydrogen detector having a substrate with the PdTi alloy deposited thereon.

DESCRIPTION OF PREFERRED EMBODIMENTS

As mentioned above, metal alloys according to embodiments of the present invention incorporate palladium and titanium.

The base metal of the alloy is palladium. Palladium is capable of absorbing hydrogen. Additionally, is able to diffuse through palladium readily. As discussed above, palladium, alone, is not a suitable hydrogen sensor. Olsen et al. in "Palladium and Titanium Thin Films as Probes for Determination of Hydrogen in Helium," *Anal. Chem.*, Vol. 49, No. 6, 1977, indicate that titanium is also capable of absorbing hydrogen. The hydrogen, however, does not migrate as readily through the titanium. Yoshihara et al. in "The Diffusivity of Hydrogen in Palladium-Based Solid Solutions," *Acta. Metall.*, Vol. 30, 1982 disclose that the inclusion of titanium will decrease mobility of hydrogen in palladium.

According to embodiments of the present invention, alloys of PdTi can be prepared which exhibit greater changes in electrical resistivity when exposed to concentrations of hydrogen. With greater changes in resistivity at lower concentrations of hydrogen, the PdTi alloys according to embodiments of the present invention are more reliable in detecting the presence of hydrogen.

Since both metals are hydrogen sensitive, the relative concentration of each could range from above 0 to below 100% such as 1–99:99–1%. With proper preconditioning, the alloy will still be hydrogen or hydrocarbon sensitive. The exact alloy ratio used will depend on the application. If the sensor will be exposed to high concentrations of hydrogen, the amount of Ti in the alloy will be increased. If the sensor needs to detect hydrogen at low concentrations, the amount of Pd in the alloy will be increased. In preferred embodiments, the alloy contains between 50 or 60 and 99 atomic % Pd. In a preferred form, the alloy contains between 70 and 98 atomic % Pd. In another preferred form, the alloy contains between 90 and 98 atomic % Pd.

According to one embodiment of the present invention, the PdTi alloy is formed by sputtering. Atomic particles of palladium and titanium are shot from separate targets (although a single target, can be used) onto a substrate. The sputtering rates can be varied to vary the amount of each material present in the alloy. The Pd can be sputtered at a power between 50 W and 450 W. In the preferred form, the Pd is sputtered at a power between 75 W and 300 W. In the more preferred form, the Pd is sputtered a power between 100 W and 200 W.

Since the Ti is oxygen sensitive, the amount of Ti in the alloy will also depend on the desire to track the oxygen concentration simultaneously. The Ti can be sputtered at a power between 25 W and 250 W. In the preferred form, the Ti is sputtered at a rate between 50 W and 150 W. In the preferred form, the amount of palladium in the alloy is greater than the amount of titanium. For hydrogen sensing applications in environments which vary from inert hydrogen to air, a preferred power ratio of Pd/Ti is 150 W/50 W which corresponds to approximately 95.6 atomic % Pd and 4.4 atomic % Ti.

Additional materials may be present in the alloy. These additives include other materials which are oxygen or hydrogen sensitive. The additives may also provide sensitivity to other gases. These additives include elements such as Cr, Ru, Ag, Au, Zr, Cu, Ir, Al or Hf. In preferred embodiments, the alloy may contain up to 20 atomic % of these elements. Other additives including Pt and Ni may also be used. Alloys containing these additives may have less than or greater than 20 atomic % of Pt or Ni.

The sputtered particles adhere to the substrate 1 and form a thin film layer 3 on a surface 2 of the substrate. A thin layer is preferred to maximize response and recovery time. For example, the thin layer may have a thickness up to 3000 angstroms. A layer that is on the order of 5000 angstroms may result in cracking of the layer. A large number of materials may be used as a substrate. If the user wishes to provide an oxygen reservoir for the Ti, then an oxide such as $Al_2O_3$ or $SiO_2$ may be used. If the migration of hydrogen into layers beneath the alloy is to be avoided, then a layer of $Si_3N_4$ or Au may be employed. For high temperature applications, the use of SiC as a semiconductor or a substrate may be used. With SiC as a substrate, the sensor structure may be heated to at least 600° C. At these temperatures, hydrocarbons disassociate and are detectable. The addition of Ti allows the alloy to act like a catalyst. This structure should be able to detect hydrocarbons in an oxygen concentration varying environment.

The thin film may be annealed to ensure that the palladium and titanium are evenly distributed throughout the alloy. The annealing process also removes impurities from the surface of the film which may affect the resistivity of the alloy. The sample may be annealed in air, inert environments, or in a vacuum for several hours or for several days at temperatures from 100° C. to at least 500° C.

In a hydrogen detector containing the PdTi alloy shown in the FIGURE, the thin film layer 3 is connected to electrical circuitry 4. Changes in the electrical resistance of the thin film layer of PdTi alloy are detected by the electrical circuitry 4 to indicate the presence of hydrogen.

EXAMPLE 1

A thin film of the PdTi metal alloy is deposited on a substrate using two gun sputtering. The palladium and titanium particles are shot from separate targets onto the substrate. The palladium and titanium are sputtered at power of 100 w and 50 w respectively. This produces an alloy containing approximately 90.6 atomic % Pd and 9.4 atomic % Ti. The film is then annealed at 250° C. overnight (i.e., approximately 12 hours). The film in an environment of 100 % hydrogen experiences a change in resistance of near 16 to 18%. As the hydrogen concentration is decreased, the resistance of the alloy returns to near the base line resistance (i.e., the resistance of the alloy prior to exposure to hydrogen).

EXAMPLE 2

The same procedure as in Example 1 is repeated except that the palladium and titanium are sputtered at power of 300 W and 50 W respectively, which yields approximately 98.9 atomic % Pd and 1.1 atomic % Ti. Furthermore, the film is not annealed. When exposed in an environment of 100% hydrogen, this alloy experiences a change in resistance near 8%.

EXAMPLE 3

A thin film of the PdTi metal alloy is deposited on a substrate using two gun sputtering with the palladium and titanium sputtered at power of 150 W and 50 W respectively. This produces an alloy containing approximately 95.6 atomic % Pd and 4.4 atomic % Ti. The response of the film is then measured in 100% hydrogen recovering in air and in nitrogen. After an initial cycling in hydrogen, the resistance change of the alloy to 100% hydrogen is near 6% when measured in flowing nitrogen. The cycling in hydrogen changes the baseline by less than 0.8% over 3 cycles.

The sample is then annealed in-situ at 250° C. in air for four days. The sensor properties improve dramatically. The resistance changes at room temperature in 100% hydrogen by approximately 16% with a very stable recovery to a baseline in air. The sample is then exposed to 100% hydrogen and allowed to recover in pure nitrogen. The baseline in nitrogen is slightly higher than that in air (near 1%) but recovers to the air resistance baseline value after exposure to air. The change in resistance of the alloy is repeatable when repeatedly exposed to environments of hydrogen.

EXAMPLE 4

A thin film of the PdTi metal alloy is deposited on a substrate using two gun sputtering with the palladium and titanium sputtered at power of 200 W and 200 W respectively. This produces an alloy containing approximately 71 atomic % Pd and 29 atomic % Ti. The alloy has a 1% resistance change to exposure of up to 100% hydrogen as sputtered. After annealing for 4 hours at 295° C., the alloy changes resistance by approximately 7% upon exposure to 100% hydrogen.

EXAMPLE 5

A thin film of the PdTi metal alloy is deposited on a substrate using two gun sputtering with the palladium and titanium sputtered at power of 400 W and 100 W respectively. This produces an alloy containing approximately 96.3 atomic % Pd and 3.7 atomic % Ti. The alloy is heated to 100° C. overnight in air, reduced to 35° C., and then exposed to 100% hydrogen. The sensor has a large resistance change (approximately 33%) but also has a large increase in the baseline resistance value (approximately 25%). This indicates a hydrogen induced phase change. The alloy temperature is returned to 100° C. and then cycled in an environment of 100% hydrogen then air. The resistance change in 100% hydrogen is reduced to 5% at this temperature. The alloy exhibits a slight drift in baseline resistance but there is no indication of a phase change at the higher temperature.

EXAMPLE 6

A thin film of the PdTi metal alloy is deposited on a substrate using two gun sputtering with the palladium and titanium sputtered at power of 200 W and 50 W respectively. This produces an alloy containing approximately 97.5 atomic % Pd and 2.5 atomic % Ti. After an initial exposure up to 100% hydrogen, the alloy is then exposed to increasing concentrations of hydrogen. The alloy is exposed to environments having 10%, 50% and 100% hydrogen. The alloy experiences a resistance change by 5.5%, 11.76% and 16.7% respectively. The alloy is a reliable indicator at low concentrations of hydrogen.

The invention has been described with reference to the embodiments and examples thereof which are intended to be illustrative. Various changes and modifications may be made without departing from the spirit and scope of the invention as defined in the following claims.

The invention claimed is:

1. A hydrogen detector comprising:
    a substrate;
    a thin film of PdTi metal alloy deposited on said substrate, wherein said PdTi alloy contains between 50 and 99 atomic % Pd and between 1 and 50% Ti, and wherein the PdTi alloy experiences a change in electrical resistance when exposed to hydrogen; and
    electrical circuitry connected to said PdTi thin film, wherein said change in resistance is detected by said electrical circuitry.

2. The hydrogen detector according to claim 1, wherein the PdTi alloy experiences a change in resistivity of at least about 5% when exposed to an environment of 10% hydrogen.

3. The hydrogen detector according to claim 1, wherein the PdTi alloy experiences a change in resistivity at least 10% when exposed to an environment of 100% hydrogen.

4. The hydrogen detector according to claim 1, wherein said thin film of PdTi forms a gate of a metal oxide semiconductor field effect transistor and said electrical circuitry is connected to said MOSFET.

5. The hydrogen detector according to claim 1, wherein said thin film of PdTi forms a gate of a Schottky diode structure and said electrical circuitry is connected to said Schottky diode.

6. A method of forming a hydrogen detector, comprising the steps of: providing a substrate;

depositing a thin film of PdTi alloy on the substrate wherein the PdTi alloy contains between 50 and 99 atomic % Pd and between 1 and 50% Ti; and connecting electrical circuitry to said thin film of PdTi alloy, whereby change in the resistance in said thin film of PdTi alloy is detected by said electrical circuitry.

7. The method according to claim 6, wherein the PdTi alloy experiences a change in resistivity of at least about 5% when exposed to an environment of 10% hydrogen.

8. The method according to claim 6, wherein the PdTi alloy experiences a change in electrical resistance of at least 10% when exposed to an environment of 100% hydrogen.

9. The method according to claim 6, wherein the thin film of PdTi alloy is deposited by sputtering.

10. The method according to claim 9, wherein the PdTi alloy is deposited by separately sputtering Pd and Ti from separate targets.

11. The method according to claim 10, wherein the Ti is sputtered at a power of between 25 W and 250 W.

12. The method according to claim 11, wherein the Ti is sputtered at a power of between 50 W and 150 W.

13. The method according to claim 10, wherein the Pd is sputtered at a power of between 50 W and 450 W.

14. The method according to claim 13, wherein the Pd is sputtered at a power of between 75 W and 300 W.

15. The method according to claim 14, wherein the Pd is sputtered at a power of between 100 W and 200 W.

16. A method for detecting hydrogen and hydrocarbons, comprising the steps of:

providing a substrate having a thin film of PdTi alloy thereon;

connecting electrical circuitry to said thin film of PdTi alloy;

detecting changes in electrical resistance in said PdTi alloy by means of said electrical circuitry to indicate the presence of hydrogen and hydrocarbons.

17. The method according to claim 16, wherein the PdTi structure and said electrical circuitry is connected to said Schottky diode.

18. The method according to claim 16, wherein the PdTi alloy experiences a change in electrical resistance of at least 5% when exposed to an environment of 10% hydrogen.

* * * * *